(12) United States Patent
Serhan et al.

(10) Patent No.: US 7,429,378 B2
(45) Date of Patent: Sep. 30, 2008

(54) TRANSDISCAL ADMINISTRATION OF HIGH AFFINITY ANTI-MMP INHIBITORS

(75) Inventors: Hassan Serhan, South Easton, MA (US); Thomas M. DiMauro, Southborough, MA (US); Mohamed Attawia, Canton, MA (US); Sudhakar Kadiyala, South Easton, MA (US); David Urbahns, Barrington, RI (US); Scott Bruder, Sudbury, MA (US); Laura J. Brown, Hamilton Square, NJ (US); Jeffrey C. Geesin, Doylestown, PA (US)

(73) Assignee: DePuy Spine, Inc., Raynham, MA (US)

( * ) Notice: Subject to any disclaimer, the term of this patent is extended or adjusted under 35 U.S.C. 154(b) by 631 days.

(21) Appl. No.: 10/610,355

(22) Filed: Jun. 30, 2003

(65) Prior Publication Data

US 2004/0228853 A1 Nov. 18, 2004

Related U.S. Application Data

(63) Continuation-in-part of application No. 10/456,948, filed on Jun. 6, 2003.

(60) Provisional application No. 60/470,098, filed on May 13, 2003.

(51) Int. Cl.
*A61K 35/00* (2006.01)

(52) U.S. Cl. ................................... 424/94.65
(58) Field of Classification Search ............... 424/94.65
See application file for complete search history.

(56) References Cited

U.S. PATENT DOCUMENTS

| | | | |
|---|---|---|---|
| 3,678,158 A | 7/1972 | Sussman | |
| 4,341,867 A | 7/1982 | Johansen | |
| 4,427,649 A | 1/1984 | Dingle et al. | |
| 4,435,506 A | 3/1984 | Jackson et al. | |
| 4,696,816 A | 9/1987 | Brown | |
| 5,095,037 A | 3/1992 | Iwamitsu et al. | |
| 5,116,964 A | 5/1992 | Capon et al. | |
| 5,194,596 A | 3/1993 | Tischer et al. | |
| 5,223,248 A | 6/1993 | McNamara et al. | |
| 5,225,538 A | 7/1993 | Capon et al. | |
| 5,231,024 A | 7/1993 | Moeller et al. | |
| 5,258,371 A | 11/1993 | Golub et al. | |
| 5,270,300 A | 12/1993 | Hunziker | |
| 5,368,841 A | 11/1994 | Trauner et al. | |
| 5,447,851 A | 9/1995 | Beutler et al. | |
| 5,510,370 A | 4/1996 | Hock | |
| 5,656,272 A | 8/1997 | Le et al. | |
| 5,656,644 A | 8/1997 | Adams et al. | |
| 5,728,396 A | 3/1998 | Peery et al. | |
| 5,833,984 A | 11/1998 | Eibl et al. | |
| 5,942,499 A | 8/1999 | Radomsky | |
| 5,965,583 A | 10/1999 | Beers et al. | |
| 6,049,026 A | 4/2000 | Muschler | |
| 6,277,969 B1 | 8/2001 | Le et al. | |
| 6,284,471 B1 | 9/2001 | Le et al. | |
| 6,340,369 B1 | 1/2002 | Ferree | |
| 6,352,557 B1 | 3/2002 | Ferree | |
| 6,419,944 B2 * | 7/2002 | Tobinick | 424/422 |
| 6,541,477 B2 | 4/2003 | Lewicki et al. | |
| 6,554,830 B1 | 4/2003 | Chappius | |
| 6,590,081 B1 | 7/2003 | Zhang | |
| 6,623,472 B1 | 9/2003 | Reincke et al. | |
| 6,713,246 B1 | 3/2004 | Reinecke et al. | |
| 6,756,215 B1 | 6/2004 | Wolfraim et al. | |
| 2001/0006948 A1 | 7/2001 | Kang et al. | |
| 2001/0016195 A1 | 8/2001 | Tobinick | |
| 2001/0026801 A1 | 10/2001 | Tobinick | |
| 2002/0010471 A1 | 1/2002 | Wironen et al. | |
| 2002/0026244 A1 | 2/2002 | Trieu | |
| 2002/0032155 A1 | 3/2002 | Ferree | |
| 2002/0082697 A1 | 6/2002 | Damien | |
| 2002/0107200 A1 | 8/2002 | Chang et al. | |
| 2002/0169162 A1 | 11/2002 | Smith et al. | |
| 2002/0198599 A1 | 12/2002 | Haldimann | |
| 2003/0007972 A1 | 1/2003 | Tobinick | |
| 2003/0039651 A1 | 2/2003 | Olmarker | |
| 2003/0049256 A1 | 3/2003 | Tobinick | |
| 2003/0069639 A1 | 4/2003 | Sander et al. | |
| 2003/0134792 A1 | 7/2003 | Pike et al. | |
| 2003/0207827 A1 | 11/2003 | Boyle et al. | |
| 2004/0022864 A1 | 2/2004 | Freyman et al. | |
| 2004/0126372 A1 | 7/2004 | Banerjee et al. | |

(Continued)

FOREIGN PATENT DOCUMENTS

EP 0 218 868 A2 4/1987

(Continued)

OTHER PUBLICATIONS

Haro et al J. Clinical Investigation (2000) 100(2) pp. 143-150.*

(Continued)

*Primary Examiner*—Ardin H. Marschel
*Assistant Examiner*—Shirley V Gembeh
(74) *Attorney, Agent, or Firm*—Hamilton, Brook, Smith & Reynolds, P.C.

(57) ABSTRACT

The present invention relates to injecting a high affinity antagonist of MMPs into a diseased intervertebral disc.

29 Claims, No Drawings

U.S. PATENT DOCUMENTS

| | | |
|---|---|---|
| 2004/0193274 A1 | 9/2004 | Trieu |
| 2004/0229786 A1 | 11/2004 | Attawia et al. |
| 2004/0229878 A1 | 11/2004 | DiMauro et al. |
| 2005/0025765 A1 | 2/2005 | DiMauro et al. |
| 2005/0038001 A1 | 2/2005 | Attawia et al. |
| 2005/0100538 A1 | 5/2005 | Attawia et al. |
| 2005/0112091 A1 | 5/2005 | DiMauro et al. |
| 2007/0237777 A1 | 10/2007 | DiMauro et al. |

FOREIGN PATENT DOCUMENTS

| | | |
|---|---|---|
| EP | 0 288 088 B1 | 10/1988 |
| EP | 0 438 234 A1 | 7/1991 |
| EP | 0 950 417 A2 | 10/1999 |
| EP | 1 133 995 A2 | 9/2001 |
| EP | 1 153 607 A2 | 11/2001 |
| EP | 1 464 307 A1 | 10/2004 |
| WO | WO 91/02078 A1 | 2/1991 |
| WO | WO 92/07076 A1 | 4/1992 |
| WO | WO 92/16553 A1 | 10/1992 |
| WO | WO 93/16099 A2 | 8/1993 |
| WO | WO 97/28828 A1 | 8/1997 |
| WO | WO 98/24477 A1 | 6/1998 |
| WO | WO 99/45923 A1 | 9/1999 |
| WO | WO 01/85179 A2 | 11/2001 |
| WO | WO 02/057240 A1 | 7/2002 |
| WO | WO 02/100387 | * 12/2002 |
| WO | WO 02/100387 A1 | 12/2002 |
| WO | WO 03/ 000190 A2 | 1/2003 |
| WO | WO2004/022078 A1 | 3/2004 |
| WO | WO 2005/000283 A2 | 1/2005 |
| WO | WO 2005/110276 A1 | 11/2005 |
| WO | WO 2006/031376 A2 | 3/2006 |

OTHER PUBLICATIONS

Goupille et al. (Spine) V. 23(14) 1612-1626 (1998).*
Ohno et al. Anaesth. Analg 1997; 85:1312-1316.*
Ahn, N.U., et al., "Effect of Nutrient Concentration and OP-1 on the Metabolism of Intervertebral Disc: In Vitro Organ Culture Study," 28, Abstracts of the 30th Annual Meeting of the International Society for the Study of the Lumbar Spine, Vancouver, Canada (May 2003).
Allali, F. et al., "Increase in Bone Mineral Density of Patients with Spondyloarthropathy Treated with Anti-Tumour Necrosis Factor α," *Ann. Rheum. Dis.*, 62:347-349 (2003).
Andonopoulos, A.P., et al., "Intra-articular Anti-Tumor Necrosis Factor α Antibody in Recalcitrant Arthritis of Behcet's Disease," *Clinical and Experimental Rheumatology 21*(4 Suppl 30): S-57-S58 (Jul.-Aug. 2003).
Arai, I., et al., "Pretreatment with Loxoprofen Sodium, 6-OHDA or Anti TNF-Alpha Antibody Reduce Fos-Like Immunoreactivity in Rat Experimental Lumber Disc Herniation," 111, Abstracts of the 30th Annual Meeting of the International Society for the Study of the Lumbar Spine, Vancouver, Canada (May 2003).
Ariga, K., et al., "Mechanical Stress-Induced Apoptosis of Endplate Chondrocytes in Organ-Cultured Mouse Intervertebral Discs," *Spine*, 28(14):1528-1533 (2003).
Ashkenazi, A., et al., "Protection Against Endotoxic Shock by a Tumor Necrosis Factor Receptor Immunoadhesin," *Proc. Natl. Acad. Sci. USA*, 88:10535-10539 (1991).
Baker, D., et al. "Control of Established Experimental Allergic Encephalomyelitis by Inhibition of Tumor Necrosis Factor (TNF) Activity Within the Central Nervous System Using Monoclonal Antibodies and TNF Receptor-Immunoglobulin Fusion Proteins," *Eur. J. Immunol.*, 24:2040-2048 (1994).
Biskobing, D.M., "Novel Therapies for Osteoporosis," *Expert Opinion Invest. Drugs*, 12(4):611-621 (2003).
Boehm, J.C., et al., "New Inhibitors of p38 Kinase," *Exp. Opin, Ther. Patents*, 10(1):25-37 (2000).
Bokarewa, M., et al., "Local Infusion of Infliximab for the Treatment of Acute Joint Inflammation," *Ann. Rheum Dis.*, 62: 783-784 (2003).
Braun, J. And Sieper, J., "Overview of The Use of The Anti-TNF Agent Infliximab in Chronic Inflammatory Diseases," *Expert Opin. Biol. Ther.*, 3(1):141-168 (2003).
Braun, J., et al., "Anti-Tumor Necrosis Factor α Therapy for Ankylosing Spondylitis: International Experience," *Ann. Rheum. Dis.*, 61(Supp. III):iii51-iii60 (2002).
Bringman, T.S., et al., "Monoclonal Antibodies to Human Tumor Necrosis Factors Alpha and Beta: Application for Affinity Purification, Immunoassays, and as Structural Probes," *Hybridoma*, 6(5):489-507 (1987).
Burke, J. G., et al., "Human Nucleus Pulposus Secretes Transforming Growth Factor Beta-1 and Basic Fibroblast Growth Factor," 189, Abstracts of the 30th Annual Meeting of the International Society for the Study of the Lumbar Spine, Vancouver, Canada (May 2003).
Butler, D.M., et al., "TNF Receptor Fusion Proteins are Effective Inhibitors of TNF-Mediated Cytotoxicity on Human KYM-1D4 Rhabdomyosarcoma Cells," *Cytokine*, 6(6):616-623 (1994).
Capon, D.J., et al. "Designing CD4 Immunoadhesins for AIDS Therapy," *Nature*, 337:525-531 (1989).
Cardone, D.A., et al., "Diagnostic and Therapeutic Injection of the Hip and Knee," *Family Medicine*, 67(10):2147-2152 (2003).
Cirillo, P.F., et al., "The Non-Diaryl Heterocycle Classes of p38 MAP Kinase Inhibitors," *Current Topics in Medicinal Chemistry*, 2:1021-1035 (2002).
Connolly, J., et al., "Development of an Osteogenic Bone-Marrow Preparation," *The Journal of Bone and Joint Surgery, Inc.*, 71-A (5): 684-691 (1989).
Conti, F., et al., "Successful Treatment with Intraarticular Infliximab for Resistant Knee Monarthritis in a Patient with Spondylarthropathy," *Arthritis & Rheumatism*, 52(4): 1224-1226 (2005).
Corcoran, A.E., et al., "Characterization of Ligand Binding by the Human p55 Tumour-Necrosis-Factor Receptor," *Eur. J. Biochem.*, 223:831-840 (1994).
Cornefjord, M., et al., "Cerebrospinal Fluid Biomarkers in Experimental Spinal Nerve Root Injury," 38, Abstracts of the 30th Annual Meeting of the International Society for the Study of the Lumbar Spine, Vancouver, Canada (May 2003).
Crandall, C., "Combination Treatment of Osteoporosis: A Clinical Review," *J. of Women's Health & Gender-Based Medicine*, 11(3):211-224 (2002).
Dayer, J.M., "The Pivotal Role of Interleukin-1 in the Clinical Manifestations of Rheumatoid Arthritis," *Rheumatology, Oxford University Press*, London, GB, 42(Suppl 2):ii3-ii10 (2003).
DeSantis, A. and Buchman, A..., "Current and Emerging Therapies in Osteoporosis," *Expert Opin. Pharmacother.*, 3(7):835-843 (2002).
Diwan, A.D., et al., "Current Concepts in Intervertebral Disk Restoration," *Tissue Engineering in Orthopedic Surgery*, 31(3):453-464 (2000).
Edwards, S. L., et al., "Radiographic Assessment of Posterolateral Spine Fusion With and Without Platelet Rich Plasma," 117, Abstracts of the 30th Annual Meeting of the International Society for the Study of the Lumbar Spine, Vancouver, Canada (May 2003).
Engelmann, H., et al., "Two Tumor Necrosis Factor-Binding Proteins Purified From Human Urine," *J. Biol. Chem.*, 265(3):1531-1536 (1990).
Ezra, A. and Golomb, G., "Administration Routes and Delivery Systems of Bisphosphonates for the Treatment of Bone Resorption," *Adv. Drug Del. Rev.*, 42:175-195 (2000).
Fendly, B.M., et al., "Murine Monoclonal Antibodies Defining Neutralizing Epitopes on Tumor Necrosis Factor," *Hybridoma*, 6:359-370 (1987).
Frain, J., et al., "Use of cDNA Microarrays to Investigate Cytokine Expression in Intervertebral Disc Degeneration," 126, Abstracts of the 30th Annual Meeting of the International Society for the Study of the Lumbar Spine, Vancouver, Canada (May 2003).
Gabay, C., "IL-1 Trap," *Curr. Opin. Invest. Drugs, Curr. Drugs*, London, GB, 4(5):593-597 (2003).
Ganey, T.M. and Meisel, H.J., "A Potential Role for Cell-Based Therapeutics in the Treatment of Intervertebral Disc Herniation," *Eur. Spine J.*, 11 (Suppl. 2): S206-S214 (2002).

Goodman, S., et al., "Effects of Local Infusion of TGFβ on Bone Ingrowth in Rabbit Chambers," *J. Biomed. Mat. Res. (Appl Biomater)*, 53:475-479 (2000).

Kawakami, M., et al., "Role of IL-8, MCP-1 and PH in Neuropathic Pain Enhanced by Degenerative Nucleus Pulposus," 127, Abstracts of the 30th Annual Meeting of the International Society for the Study of the Lumbar Spine, Vancouver, Canada (May 2003).

Hirai, M., et al., "Production and Characterization of Monoclonal Antibodies to Human Tumor Necrosis Factor," *J. Immunol. Meth.*, 96:57-62 (1987).

Hunter, C.J., et al., "Functional Behavior of Notochordal Cell Clusters in the Canine Nucleus Pulposus: Cell Communication and Survival," 70, Abstracts of the 30th Annual Meeting of the International Society for the Study of the Lumbar Spine, Vancouver, Canada (May 2003).

Hydrogels, Encyclopedia of Polymer Science and Technology, vol. 2, (Wiley and Sons, 2003).

Igarashi, A., et al., "Inflammatory Cytokines Release From Facet Joint Tissue in Degenerative Lumbar Disorders," 262, Abstracts of the 30th Annual Meeting of the International Society for the Study of the Lumbar Spine, Vancouver, Canada (May 2003).

Imai, Y., et al., "Effect of Recombinant Human Osteogenic Protein-1 on Extracellular Matrix Metabolism by Human Annulus Fibrosus and Nucleus Pulposus Cells," 205, Abstracts of the 30th Annual Meeting of the International Society for the Study of the Lumbar Spine, Vancouver, Canada (May 2003).

Imai, Y., et al., "The Quantification of Cytokine-Induced Matrix Catabolism in Tissue Engeneered Intervertebral Discs," 67, Abstracts of the 30th Annual Meeting of the International Society for the Study of the Lumbar Spine, Vancouver, Canada (May 2003).

Inui, Y., et al., "Fas-Ligand Expression on Nucleus Pulposus Cells Begins in Developing Embryo," 42, Abstracts of the 30th Annual Meeting of the International Society for the Study of the Lumbar Spine, Vancouver, Canada (May 2003).

Kato, H., et al., "The Effect of IL-1 on the Rabbit Intervertebral Disc In Vivo," 199, Abstracts of the 30th Annual Meeting of the International Society for the Study of the Lumbar Spine, Vancouver, Canada (May 2003).

Kimble, R.B., et al., "Estrogen Deficiency Increases the Ability of Stromal Cells to Support Murine Osteoclastogenesis Via an InterLeukin-1 and Tumor Necrosis Factor-Mediated Stimulation of Macrophage Colony-Stimulating Factor Production," *J. Biol. Chem.*, 271(46):28890-28897 (1996).

Kimble, R.B., et al., "The Functional Block of TNF but Not of IL-6 Prevents Bone Loss in Ovariectomized Mice," *J. Bone Min. Res.*, 12(6):935-941 (1997).

Koch, H., et al., "Spontaneous Secretion of Interleukin 1 Receptor Antagonist (IL-1Ra) by Cells Isolated from Herniated Lumbar Discal Tissue After Discectomy," *Cytokine*, 10(9): 703-705 (1998).

Kolls, J., et al. "Prolonged and Effective Blockade of Tumor Necrosis Factor Activity Through Adenovirus-Mediated Gene Transfer," *Proc. Natl. Acad. Sci. USA*, 91:215-219 (1994).

Korhonen, T., et al., "Efficacy of Infliximab for Disc Herniation-Induced Sciatica One-Year Follow-Up," 14, Abstracts of the 30th Annual Meeting of the International Society for the Study of the Lumbar Spine, Vancouver, Canada (May 2003).

Kozbor, D. And Roder J., "The Production of Monoclonal Antibodies from Human Lymphocytes," *Immunol. Today*, 4(3):72-79 (1983).

Kwon, U-H., et al., "Dexamethasone Stimulates Cellular Proliferation While Downregulates Matrix Synthesis in Intervertebral Disc Cells," 29, Abstracts of the 30th Annual Meeting of the International Society for the Study of the Lumbar Spine, Vancouver, Canada (May 2003).

Lane, N.E., et al., "Basic Fibroblast Growth Factor Forms New Trabeculae that Physically Connect with Pre-Existing Trabeculae, and This New Bone is Maintained With an Anti-Resorptive Agent and Enhanced with an Anabolic Agent in an Osteopenic Rat Model," *Osteopros. Int.*, 14:374-382 (2003).

LaVan, et al., "Small-scale Systems for In Vivo Drug Delivery," *Nature Biotechnology*, 21(10): 1184-1191 (2003).

Lehman, T.J.A., et al., "Thalidomide Theraphy for Recalcitrant Systemic Onset Juvenile Rheumatoid Arthritis," *J. Pediatrics*, 140: 125-7 (2002).

Le Maitre, C. L., et al., "Expression of the IL-1 Family in Human Intervertebral Disc," 217, Abstracts of the 30th Annual Meeting of the International Society for the Study of the Lumbar Spine, Vancouver, Canada (May 2003).

Le Maitre, C. L., et al., "Response of Human Intervertebral Disc Cells to IL-1," 216, Abstracts of the 30th Annual Meeting of the International Society for the Study of the Lumbar Spine, Vancouver, Canada (May 2003).

Le Visage, C., et al., "Interaction of Human Mescenchymal Stem Cells with Disc Cells: Changes in Biosynthesis of Extracellular Matrix," 25, Abstracts of the 30th Annual Meeting of the International Society for the Study of the Lumbar Spine, Vancouver, Canada (May 2003).

Lee, J.C., et al., "Inhibition of p38 MAP Kinase as a Therapeutic Strategy," *Immunopharmacology*, 47: 185-201 (2000).

Lee, C.S., et al., "A Single Period of Hyperphysiologic Stretch Induces IL-6, TGF-beta and Cell Proliferation in Anulus FIbrosus Cells," 215, Abstracts of the 30th Annual Meeting of the International Society for the Study of the Lumbar Spine, Vancouver, Canada (May 2003).

Lesslauer, W. et al., "Recombinant Soluble Tumor Necrosis Factor Receptor Proteins Protect Mice From Lipopolysaccharide-induced Lethality," *Eur. J. Immunol.*, 21:2883-2886 (1991).

Li, J., et al., "The Effects of Bone Morphogenetic Protein 2 (BMP-2) and Cartilage-Derived Morphogentic Protein 2 (CDMP-2) on Aggrecan Gene Expression in Chondrocytes," 30, Abstracts of the 30th Annual Meeting of the International Society for the Study of the Lumbar Spine, Vancouver, Canada (May 2003).

Liang, C.-M., et al., "Production and Characterization of Monoclonal Antibodies Against Recombinant Human Tumor Necrosis Factor/Cachectin," *Biochem. Biophys. Res. Comm.*, 137:847-854 (1986).

Loetscher, H., et al., "Molecular Cloning and Expression of the Human 55 kd Tumor Necrosis Factor Receptor," *Cell*, 61:351-359 (1990).

Lotz, J. C., et al., "Cytokines in Normal, Degenerated, and Nucleoplasty-Treated Porcine Discs," 157, Abstracts of the 30th Annual Meeting of the International Society for the Study of the Lumbar Spine, Vancouver, Canada (May 2003).

Maeda, S. and Kokubun, S., "Changes With Age in Proteoglycan Synthesis in Cells Cultured In Vitro From the Inner and Outer Rabbit Annulus Fibrosus," *Spine*, 25(2):166-169 (2000).

Meager, A. et al., "Preparation and Characterization of Monoclonal Antibodies Directed Against Antigenic Determinants of Recombinant Human Tumour Necrosis Factor (rTNF)," *Hybridoma*, 6(3):305-311 (1987).

Meijer, H., et al., "The Production of Anti-Inflammatory Cytokines in Whole Blood by Physico-Chemical Induction," *Inflamm. Res.*, 52:404-407 (2003).

Miyamoto, H., et al., "The Effect of Mechanical Stress on the Production of Inflammatory Agents by Disc Cells," 110, Abstracts of the 30th Annual Meeting of the International Society for the Study of the Lumbar Spine, Vancouver, Canada (May 2003).

Möller, A., et al., "Monoclonal Antibodies to Human Tumor Necrosis Factor : In Vitro and In Vivo Application," *Cytokine*, 2(3):162-169 (1990).

Molloy, T., et al., "The Roles of Growth Factors in Tendon and Ligament Healing," *Sports Med.* 33(5): 381-394 (2003).

Müller, R., "Determination of Affinity and Specificity of Anti-Hapten Antibodies by Competitive Radioimmunoassay," *Meth. Enzymol.*, 92:589-601 (1983).

Nakamura, K., et al., "Local Application of Basic Fibroblast Growth Factor into the Bone Increases Bone Mass at the Applied Site in Rabbits," *Arch. Orthop. Trauma Surg.*, 115:344-346 (1996).

Nakamura, K., et al., "Stimulation of Endosteal Bone Formation by Local Intraosseous Application of Basic Fibroblast Growth Factor in Rats," *Rev. Rhum. [Engl. Ed.]*, 64(2):101-105 (1997).

Nikas, S.N., et al., "Treatment of Resistant Rhematoid Arthritis by Intra-Articular Infliximab Injections: A Pilot Study," *Ann Rheum Dis* 63: 102-103 (2004).

Ohtori, S., et al., "TNF-α and TNF-α Receptor 1 Upregulation in GLIA and Neurons After Nerve Injury. Studies in Murine DRG and Spinal Cord," 13, Abstracts of the 30th Annual Meeting of the International Society for the Study of the Lumbar Spine, Vancouver, Canada (May 2003).

Ohtori, S., et al., "TNF-α-Deficient Mice Have Fewer Macrophages in Injured Nerve and Reduced Glial Activation in DRG and Spinal Cord," 250, Abstracts of the 30th Annual Meeting of the International Society for the Study of the Lumbar Spine, Vancouver, Canada (May 2003).

Okuma, M., et al., "Rotary Cell Culture System Stimulates Annulus Fibrosus Cell Proliferation but Suppresses Proteoglycan Metabolism," 164, Abstracts of the 30th Annual Meeting of the International Society for the Study of the Lumbar Spine, Vancouver, Canada (May 2003).

Pacifici, R., "Editorial: Cytokines, Estrogen, and Postmenopausal Osteoporosis-The Second Decade," *Endocrinology*, 139(6):2659-2661 (1998).

Pederson, A.W., et al., "Thermal Assembly of a Biomimetic Mineral/Collagen Composite," *Biomaterials*, 24:4881-4890 (2003).

Peppel, K., et al. "A Tumor Necrosis Factor (TNF) Receptor-IgG Heavy Chain Chimeric Protein as a Bivalent Antagonist of TNF Activity," *J. Exp. Med.*, 174:1483-1489 (1991).

Richardson, S., et al., "Human Bone Marrow Mesenchymal Stromal Cells as a Source of Chondrocytes for Treatment of Intervertebral Disc Degeneration," 27, Abstracts of the 30th Annual Meeting of the International Society for the Study of the Lumbar Spine, Vancouver, Canada (May 2003).

Risbud, M. V., et al., "Mesenchymal Stem Cells Respond to Their Microenvironment In Vitro to Assume Nucleus Pulposus-Like Phenotype," 26, Abstracts of the 30th Annual Meeting of the International Society for the Study of the Lumbar Spine, Vancouver, Canada (May 2003).

Rodan, G.A. and Martin, T.J., "Therapeutic Approaches to Bone Diseases," *Science*, 289:1508-1514 (2000).

Sakai, D., et al., "Autologous Transplantation of Mesenchymal Stem Cells for Disc Repair," 24, Abstracts of the 30th Annual Meeting of the International Society for the Study of the Lumbar Spine, Vancouver, Canada (May 2003).

Sakai, D., et al., "Transplantation of Mesenchymal Stem Cells Embedded in Atelocollagen® Gel to the Intervertebral Disc: A Potential Therapeutic Model for Disc Degeneration," *Biomaterials*, 24: 3531-3541 (2003).

Schall, T.J., et al., "Molecular Cloning and Expression of a Receptor for Human Tumor Necrosis Factor," *Cell*, 61:361-370 (1990).

Schatteman, L., et al., "Treatment of Refractory Inflammatory Monoarthritis in Ankylosing Spondylitis by Intraarticular Injection of Infliximab," *The Journal of Rheumatology*, 33:1 82-85 (2006).

Sobajima, S., et al., "Stem Cell Therapy for Degenerative Disc Disease: An In-Vitro Feasibility Study," 43, Abstracts of the 30th Annual Meeting of the International Society for the Study of the Lumbar Spine, Vancouver, Canada (May 2003).

Stern, S., et al., "Human Intervertebral Disc Cell Culture for Disc Disorders," *Clin. Orthop.*, 419:238-244 (2004).

Takada, T., et al., "IL-6 Production was Upregulated by Interaction Between Disc Tissue and Macrophages," 41, Abstracts of the 30th Annual Meeting of the International Society for the Study of the Lumbar Spine, Vancouver, Canada (May 2003).

Takegami, K., et al., "Osteogenic Protein-1 Enhances Matrix Replenishment by Intervertebral Disc Cells Previously Exposed to Interleukin-1," *Spine*, 27(12):1318-1325 (2002).

Tsuji, T., et al., "Age-Related Changes in M-RNA Expression of Various Regulatory Factors in Rabbit Intervertebral Disc," 81, Abstracts of the 30th Annual Meeting of the International Society for the Study of the Lumbar Spine, Vancouver, Canada (May 2003).

Vahle, J.L., et al., "Skeletal Changes in Rats Given Daily Subcutaneous Injections of Recombinant Human Parathyroid Hormone (1-34) for 2 Years and Relevance to Human Safety," *Toxicol. Pathol.*, 30(3):312-321 (2002).

Weiler, C., et al., "Expression of TNF-α in Autopsy and Biopsy Specimens of Intervertebral Discs of Various Age and Degeneration," 233, Abstracts of the 30th Annual Meeting of the International Society for the Study of the Lumbar Spine, Vancouver, Canada (May 2003).

Xie, X., et al., "Treatment of Spondylodiscitis Intravenous Versus Percutaneous Intradiscal Applications of Antibiotics: An Experimental Study in Rabbits," 120, Abstracts of the 30th Annual Meeting of the International Society for the Study of the Lumbar Spine, Vancouver, Canada (May 2003).

Yaffe, A., et al., "Combined Local Application of Tetracycline and Bisphosphonate Reduces Alveolar Bone Resorption in Rats," *J. Periodontol*, 74(7):1038-1042 (2003).

Yoon, S. T., et al., "LMP-1 Upregulates Proteoglycan Synthesis in Intervertebral Disc Cells Through a BMP Mediated Process," 31, Abstracts of the 30th Annual Meeting of the International Society for the Study of the Lumbar Spine, Vancouver, Canada (May 2003).

Eustice, Carol & Richard, "What is Viscosupplementation?" http://arthritis.com/od/kneetreatments/g/viscosupplement_p.htm, Dec. 9, 2005.

Wittenberg, R.H., et al., "In Vitro Release of Prostaglandins and Leukotrienes from Synovial Tissue, Cartilage, and Bone in Degenerative Joint Diseases," *Arthritis & Rheumatism* 36(10):1444-1450 (Oct. 1993).

Yabuki, S., et al., "Prevention of Compartment Syndrome in Dorsal Root Ganglia Caused by Exposure to Nucleus Pulposus," *Spine* 26(8):870-875 (2001).

Olmarker, K. and Rydevik, B., "Selective Inhibition of Tumor Necrosis Factor-α Prevents Nucleus Pulposus-Induced Thrombus Formation, Intraneural Edema, and Reduction of Nerve Conduction Velocity," *Spine*, 26(8): 863-869 (2001).

Tobinick, E. and Davoodifar, S., "Perispinal TNF-alpha Inhibition for Discogenic Pain," *Swiss Med. Wkly.*, 133:170-177 (2003).

Karppinen, J., et al., "Tumor Necrosis Factor-α Monoclonal Antibody, Infliximab, Used to Manage Severe Sciatica," *Spine*, 28(8):750-754 (2003).

Alini, M., "A Biological Approach in Treating Disc Degeneration: Not for Today, but Maybe for Tomorrow," *Eur. Spine J.*, 11 (Supp. 2):S215-S220 (2002).

Brown, K. et al., "Gelatin/Chondroitin 6-Sulfate Microspheres for the Delivery of Therapeutic Proteins to the Joint," *Arthritis. & Rheum.*, 41(12):2185-2195 (1998).

Goupille, P. et al., "Matrix MetalloproteinasesThe Clue to Intervertebral Disc Degeneration?," Spine, 23(14): 1612-1626 (1998).

Burke, J.G. et al., "Intervertebral Discs Which Cause Low Back Pain Secrete High Levels of Proinflammatory Mediators," *J. of Bone and Joint Surg. [Br]* 84-B, 196-201 (2002).

Zhang, C. et al., "Mitogen-activated Protein (MAP) Kinase Regulates Production of Tumor Necrosis Factor-α and Release of Arachidonic Acid in Mast Cells," *J. Biol. Chem.*, 272(20): 13397-13402 (1997).

Pargellis, C. et al., "Inhibition of p38 MAP Kinase by Utilizing a Novel Allosteric Binding Site," *Nature Structural Biology*, 9(4): 268-272 (2002).

Chae, H.J. et al., "The p38 Mitogen-activated Protein Kinase Pathway Regulates Interleukin-6 Synthesis in Response to Tumor Necrosis Factor in Osteoblasts," *Bone*, 28(1): 45-53 (2001).

Aoki, Y. et al., "Local Application of Disc-Related Cytokines on Spinal Nerve Roots," *Spine* 27(15): 1614-1617 (2002).

Kawakami, M. et al., "Possible Mechanism of Painful Radiculopathy in Lumbar Disc Herniation," *Clin. Orthop.*, 351:241-251 (1998).

Gordon, J.L. et al., "Metalloproteinase Inhibitors as Therapeutics," *Clin. Exp. Rheumatol.*, 11(Suppl. 8): S91-S94 (1993).

Johnson, W.H. et al., "Collagenase Inhibitors: Their Design and Potential Therapeutic Use," *J. Enzyme Inhib.*, 2:1-22 (1987).

Abstracts of the North American Spine Society 17th Annual Meeting, *The Spine Journal*: 2(5 Suppl):49S-50S (2002).

Tobinick, E.L., "Targeted Etanercept for Discogenic Neck Pain: Uncontrolled, Open-Label Results in Two Adults," *Clin. Thera.*, 25(4):1211-1218 (2003).

Hawks, D., "Alternative Medicine: Musculoskeletal System," *Clin. Tech. Small Anim. Pract.*, 17(1):41-49 (2002).

Khot, A. et al., "The Use of Intradiscal Steroid Therapy for Lumbar Spinal Discogenic Pain—A Randomized Controlled Trial," *Spine*, 29(8):833-837 (2004).

Földes, I. et al., "Trace Elements in Tissues of Normal and Vitamin D$_2$-Treated Rats," *ACTA Biol. Acad. Sci. Hung.*, 26(3-4):141-150 (1975).

Benjamin, L.E. et al., "A Plasticity Window for Blood Vessel Remodelling is Defined by Pericyte Coverage of the Preformed Endothelial Network and is Regulated by PDGF-B and VEGF," *Development*, 125:1591-1598 (1998).

Vukicevic, S. et al., "Induction of Nephrogenic Mesenchyme by Osteogenic Protein 1 (Bone Morphogenetic Protein 7)," *Proc. Natl. Acad. Sci.*, 93:9021-9026 (1996).

Moreira, A.L. et al., "Thalidomide Exerts Its Inhibitory Action on Tumor Necrosis Factor α by Enhancing mRNA Degradation," *J. Exp. Med.*, 177:1675-1680 (1993).

CN 1 647 808 A (Zhou C) Aug. 3, 2005 (abstract) World Patents Index [online]. London, GB: Derwent Publications, Ltd., Week 200621, Accession No. 2006-194507.

CN 1 569 039 A (Niu X) Jan. 26, 2005 (abstract) World Patents Index [online]. London, GB: Derwent Publications, Ltd., Week 200577, Accession No. 2005-749289.

Shiel, W.C., Ankylosing Spondylitis, MedicineNet.com [online], Sep. 2005 [retrieved on Jun. 20, 2006]. Retrieved from the Internet <URL: http://www.medicinenet.com/script/main/art.asp?articlekey=274&pf=3&page=2>.

Sampaio, E.P. et al., "Thalidomide Selectively Inhibits Tumor Necrosis Factor α Production by Stimulated Human Monocytes," *J. Exp. Med.*, 173:699-703 (1991).

Muller, G.W. et al., "Amino-Substituted Thalidomide Analogs: Potent Inhibitors of TNF-α Production," *Bioorg. Med. Chem. Lett.*, 9:1625-1630 (1999).

Teo, S.K., "Properties of Thalidomide and its Analogues: Implications for Anticancer Therapy," *AAPS Journal* 7(1):E14-E19 (2005).

Marriott, J.B. et al., "CC-3052: A Water-Soluble Analog of Thalidomide and Potent Inhibitor of Activation-Induced TNF-α Production," *J. Immunol.*, 161:4236-4243 (1998).

Tanny, G.B. et al., "Improved Filtration Technique for Concentrating and Harvesting Bacteria," *Appl. Environ. Microbiol.*, 40(2):269-273 (1980).

Raucci, A. et al., "Activation of the ERK 1/2 and p38 Mitogen-Activated Protein Kinase Pathways Mediates Fibroblast Growth Factor-Induced Growth Arrest of Chondrocytes," *J. Biol. Chem.*, 279(3):1747-1756 (2004).

Tracey, K.J. and Cerami, A., "Tumor Necrosis Factor in Metabolism of Disease: Hormonal Actions Versus Local Tissue Effects," *Nouv. Rev. Fr. Hematol.*, 34 Suppl:S37-42 (1992) (abstract).

Crevensten, G. et al., "Intervertebral Disc Cell Therapy for Regeneration: Mesenchymal Stem Cell Implantation in Rat Intervertebral Discs," *Ann. Biomed. Eng.*, 32(3):430-434 (2004).

Abbas-Ghaleb, K. et al, "Preconcentration of Selenium Compounds on a Porous Graphitic Carbon Column in View of HPLC-ICP-AES Speciation Analysis," *Anal. Bioanal. Chem.*, 377:1026-1031 (2003).

Awasthi, Y.C. et al., "Purification and Properties of Human Erythrocyte Glutathione Peroxidase," *J. Biol. Chem.*, 250(13):5144-5149 (1975).

Biemond, P. et al., "Protective Factors Against Oxygen Free Radicals and Hydrogen Peroxide in Rheumatoid Arthritis Synovial Fluid," *Arthritis Rheum.*, 27(7):760-765 (1984).

Ceponis, A. et al. "Effects of Low-Dose, Noncytotoxic, Intraarticular Liposomal Clodronate on Development of Erosions and Proteoglycan Loss in Established Antigen-Induced Arthritis in Rabbits," *Arthritis and Rheum.*, 44(8): 1908-1916 (2001).

Chan, J.M.K. et al., "Intraarticular Gene Transfer of TNFR:Fc Suppresses Experimental Arthritis with Reduced Systemic Distribution of the Gene Product," *Mol. Ther.*, 6(6): 727-736 (2002).

Desai, S. et al., "Coated Microwell Plate-Based Affinity Purification of Antigens," *Anal. Biochem.*, 328: 162-165 (2004).

Guillen, C. et al., "The Effects of Local Administration of Lactoferrin on Inflammation in Murine Autoimmune and Infectious Arthritis," *Arthritis Rheum.*, 43(9):2073-2080 (2000).

Hayashida, K. et al., "Lactoferrin Enhances Peripheral Opioid-Mediated Antinociception via Nitric Oxide in Rats," *Eur. J. Pharmacol.*, 484:175-181 (2004).

Hayashida, K. et al., "Oral Administration of Lactoferrin Inhibits Inflammation and Nociception in Rat Adjuvant-Induced Arthritis," *J. Vet. Med. Sci.*, 66(2):149-154(2004).

Kamanh, A. et al., "Plasma Lipid Peroxidation and Antioxidant Levels in Patients with Rheumatoid Arthritis," *Cell Biochem. Funct.*, 22:53-57 (2004).

Kilic, B.A. et al., "Effects of Intra-Articular Vitamin E and Corticosteroid Injection in Experimental Hemarthrosis in Rabbits," *Pediatr. Hematol. Oncol.*, 15(4):339-346 (1998).

Kim, S.H. et al. "Ex Vivo Gene Delivery of IL-1Ra and Soluble TNF Receptor Confers a Distal Synergistic Therapeutic Effect in Antigen-Induced Arthritis," *Mol. Ther.*, 6(5): 591-600 (2002).

Kurz, B. et al., "Dietary Vitamins and Selenium Diminish the Development of Mechanically Induced Osteoarthritis and Increase the Expression of Antioxidative Enzymes in the Knee Joint of STR/1N Mice," *Osteoarthritis Cartilage*, 10:119-126 (2002).

Lubberts, E. et al., "Intra-Articular IL-10 Gene Transfer Regulates the Expression of Collagen-Induced Arthritis (CIA) in the Knee and Ipsilateral Paw," *Clin. Exp. Immunol.*, 120:375-383 (2000).

Maddipati, K.R. and Marnett, L.J., "Characterization of the Major Hydroperoxide-Reducing Activity of Human Plasma," *J. Biol. Chem.*, 262(36):17398-17403 (1987).

Martinez, J.I.R., et al, "Blood Platelet Glutathione Peroxidase: Some Properties and Partial Purification," *Thromb. Res.*, 19:73-83 (1980).

Niccoli, L. et al., "Intraarticular Injection of Infliximab in Relapsing Knee Effusion in Psoriatic Arthritis: A Pilot Study," *Ann. Rheum. Dis.*, 62(1); 239-240 (2003) and EULAR—Annual European Congress of Rheumatology, Lisbon, Portugal (2003) (abstract).

Nikas, S.N., et al., "Treatment of Resistant Rheumatoid Arthritis by Intra-Articular Injections with Infliximab: A Pilot Study," *Ann. Rheum. Dis.* 62(1): 408 (2003) and EULAR—Annual European Congress of Rheumatology, Lisbon, Portugal (2003) (abstract).

Salin, M.L. and McCord, J.M., "Free Radicals and Inflammation: Protection of Phagocytosing Leukocytes by Superoxide Dismutase," *J. Clin. Invest.*, 56:1319-1323 (1975).

Schalkwijk, J. et al., "Cationization of Catalase, Peroxidase, and Superoxide Dismutase," *J. Clin. Invest.*, 76:198-205 (1985).

Steer, J.H. et al., "Altered Leucocyte Trafficking and Suppressed Tumor Necrosis Factor α Release from Peripheral Blood Monocytes After Intra-Articular Glucocorticoid Treatment," *Ann. Rheum. Dis.*, 57(12): 732-737 (1998).

Stepanik, T.M. and Ewing, D.D., "Coisolation of Glutathione Peroxidase, Catalase and Superoxide Dismutase from Human Erythrocytes," *J. Biochem. Biophys. Methods*, 20:157-169 (1990).

Tiku, M.L. et al., "Aggrecan Degradation in Chondrocytes is Mediated by Reactive Oxygen Species and Protected by Antioxidants," *Free Radic. Res.*, 30:395-405 (1999).

Tiku, M.L. et al., "Evidence Linking Chondrocyte Lipid Peroxidation to Cartilage Matrix Protein Degradation," *J. Biol. Chem.*, 275(26):20069-20076 (2000).

Trif, M. et al., "Liposomes as Possible Carriers for Lactoferrin in the Local Treatment of Inflammatory Diseases," *Exp. Biol. Med.*, 226(6):559-564 (2001).

Williams, A.S. et al., "Amelioration of Rat Antigen-Induced Arthritis by Liposomally Conjugated Methotrexate is Accompanied by Down-Regulation of Cytokine mRNA Expression," *Rheumatology*, 40:375-383 (2001).

Yang, J.G. et al., "Purification and Quantitation of a Rat Plasma Selenoprotein Distinct from Glutathione Peroxidase Using Monoclonal Antibodies," *J. Biol. Chem.*, 262(27):13372-13375 (1987).

El-Khoury, G., et al., "Percutaneous Procedures for the Diagnosis and Treatment of Lower Back Pain: Diskography, Facet-Joint Injection, and Epidural Injection," *Am. J. Roentgenol.*, 157(4): 685-691 (1991).

McMillan, D., et al., "Intra-Operative Autologous Blood Management," *Transfusion and Apheresis Science*, 27(1): 73-81 (2002).

* cited by examiner

TRANSDISCAL ADMINISTRATION OF HIGH AFFINITY ANTI-MMP INHIBITORS

RELATED APPLICATIONS

This application claims priority from U.S. Provisional Application No. 60/470,098, filed May 13, 2003, and is a continuation-in-part application of U.S. patent application Ser. No. 10/456,948, DiMauro et al., filed Jun. 6, 2003. The entire teachings of the above applications are incorporated herein by reference.

BACKGROUND OF THE INVENTION

The natural intervertebral disc contains a jelly-like nucleus pulposus surrounded by a fibrous annulus fibrosus. Under an axial load, the nucleus pulposus compresses and radially transfers that load to the annulus fibrosus. The laminated nature of the annulus fibrosus provides it with a high tensile strength and so allows it to expand radially in response to this transferred load.

In a healthy intervertebral disc, cells within the nucleus pulposus produce an extracellular matrix (ECM) containing a high percentage of proteoglycans. These proteoglycans contain sulfated functional groups that retain water, thereby providing the nucleus pulposus with its cushioning qualities. These nucleus pulposus cells may also secrete small amounts of cytokines as well as matrix metalloproteinases (MMPs). These cytokines and MMPs help regulate the metabolism of the nucleus pulposus cells.

In some instances of disc degeneration disease (DDD), gradual degeneration of the intervertebral disc is caused by mechanical instabilities in other portions of the spine. In these instances, increased loads and pressures on the nucleus pulposus cause the cells within the disc (or invading macrophages) to emit larger than normal amounts of the above-mentioned cytokines. In other instances of DDD, genetic factors or apoptosis can also cause the cells within the nucleus pulposus to emit toxic amounts of these cytokines and MMPs. In some instances, the pumping action of the disc may malfunction (due to, for example, a decrease in the proteoglycan concentration within the nucleus pulposus), thereby retarding the flow of nutrients into the disc as well as the flow of waste products out of the disc. This reduced capacity to eliminate waste may result in the accumulation of high levels of toxins that may cause nerve irritation and pain.

As DDD progresses, toxic levels of the cytokines and MMPs present in the nucleus pulposus begin to degrade the extracellular matrix. In particular, the MMPs (as mediated by the cytokines) begin cleaving the water-retaining portions of the proteoglycans, thereby reducing its water-retaining capabilities. This degradation leads to a less flexible nucleus pulposus, and so changes the loading pattern within the disc, thereby possibly causing delamination of the annulus fibrosus. These changes cause more mechanical instability, thereby causing the cells to emit even more cytokines, typically thereby upregulating MMPs. As this destructive cascade continues and DDD further progresses, the disc begins to bulge ("a herniated disc"), and then ultimately ruptures, causing the nucleus pulposus to contact the spinal cord and produce pain.

U.S. Published Patent Application No. US 2003/0039651 ("Olmarker I") teaches a therapeutic treatment of nerve disorders comprising administration of a therapeutically effective dosage of compounds, including inhibitors of MMPs.

In the examples of Olmarker I, it is taught that the therapeutic compounds are to be administered through systemic pathways. In particular, Olmarker I teaches that "the major contribution of TNF-alpha may be derived from recruited, aggregated and maybe even extravasated leukocytes, and that successful pharmacologic block may be achieved only by systemic treatment. (0133). Of note, Olmarker I appears to discourage the local addition of at least one therapeutic compound (doxycycline) to an autotransplanted nucleus pulposus to be applied to a spinal cord. (0128)

PCT Published Patent Application No. WO 02/100387 ("Olmarker II") teaches the prevention of neovascularization and/or neo-innervation of intervertebral discs by the administration of anti-angiogenic substances. Again, however, Olmarker II teaches systemic administration of these therapeutic agents.

U.S. Pat. No. 6,419,944 ("Tobinick") discloses treating herniated discs with cytokine antagonists. Tobinick teaches that local administration involves a subcutaneous injection near the spinal cord. Accordingly, Tobinick does not teach a procedure involving a sustained delivery of a drug for the treatment of DDD, nor directly administering a drug into the disc.

U.S. Published Patent Application No. 2003/0049256 (Tobinick II) discloses that injection of such therapeutic molecules to the anatomic area adjacent to the spine is accomplished by interspinous injection, and preferably is accomplished by injection through the skin in the anatomic area between two adjacent spinous processes of the vertebral column.

Tobinick II further teaches that the therapeutic compounds may be administered by interspinous injection in the human and that the dosage level is in the range of 1 mg to 300 mg per dose, with dosage intervals as short as two days. Tobinick II further discloses that other therapeutic compounds are administered in a therapeutically effective dose, which will generally be 10 mg to 200 mg per dose, and their dosage interval will be as short as once daily.

Tobinick, *Swiss Med. Weekly*, 133: 170-7 (2003) ("Tobinick III") teaches perispinal and epidural administration of TNF inhibitors.

Karppinen, *Spine*, 28(8): 750-4 (2003), teaches intravenously injecting or orally administering infliximab into patients suffering from sciatica.

As with Tobinick I and II, Karppinen does not teach a procedure involving a sustained delivery of a drug for the treatment of DDD, nor directly administering a drug into the disc space.

U.S. Pat. No. 6,352,557 (Ferree) teaches adding therapeutic substances such as anti-inflammatory medications to morselized extra-cellular matrix, and injecting that combination into an intervertebral disc. However many anti-inflammatory agents are non-specific and therefore may produce unwanted side effects upon other cells, proteins and tissue. In addition, the pain-reducing effect of these agents is typically only temporary. Lastly, these agents typically only relieve pain, and are neither curative nor restorative.

Alini, *Eur. Spine J.*, 11(Supp. 2): S215-220 (2002), teaches therapies for early stage DDD, including injection of inhibitors of proteolytic enzymes or biological factors that stimulate cell metabolic activity (i.e., growth factors) in order to slow down the degenerative process. Inhibitors of proteolytic enzymes constitute a broad class of compounds, including i) inhibitors of proteolytic enzyme synthesis and ii) inhibitors of proteolytic enzyme activity. Alini I does not specify any desired types of inhibitors of proteolytic enzymes.

U.S. Published Patent Application US 2002/0026244 ("Trieu") discloses an intervertebral disc nucleus comprising a hydrogel that may deliver desired pharmacological agents.

Trieu teaches that these pharmacological agents may include growth factors such as TGF-β and anti-inflammatory drugs, including steroids. Trieu further teaches that these pharmacological agents may be dispersed within the hydrogel having an appropriate level of porosity to release the pharmacological agent at a desired rate. Trieu teaches that these agents may be released upon cyclic loading or upon resorption.

Goupille, *Spine*, 23(14): 1612-1626 (1998) identifies Tissue Inhibitors of MMPs ("TIMPs") as degraders of MMP activity. Goupille reports that TIMP-1 and TIMP-2 bind non-covalently to active MMPs in a 1:1 molar ratio and specifically inhibit their enzymatic activity. However, Goupille also indentifies corticosteroids, retinoic acid, TGF-B, PGE1 and PGE2 as inhibitors of MMP synthesis; identifies α2-macroglobulin, hydroxamic acid, derivatives, tetracyclines and quinolones as inhibitors of MMP activity, and identifies bFGF, EGF, Retenoic acid, TGF-β, IL-6, IL-1 LIF, dexamethasone, phorbol ester, and synthetic Vitamin A analogs as stimulators of TIMPs. Moreover, as to administration route, Goupille explicitly identifies only the oral administration route.

SUMMARY OF THE INVENTION

The present inventors have developed a number of procedures for efficaciously treating degenerative disc disease by drug therapy.

In accordance with the present invention, the present inventors have developed a method of treating an intervertebral disc in which a high affinity anti-MMP compound ("HAAMMP") is administered transdiscally (directly into a degenerating disc).

There are believed to be several advantages to directly transdiscally administering HAAMMP to a targeted disc:

First, HAAMMPs inhibit the activity of MMPs. Since it is known that MMPs play primary roles in the degradation of the extracellular matrix (ECM) of the nucleus pulposus, injecting HAAMMPs directly into the disc in a therapeutically effective amount can prevent the MMPs from causing any further ECM degradation. In effect, the transdiscal adminstration of HAAMMPs helps arrest the aging process of the degenerating disc. Accordingly, the present invention seeks to treat the degenerative disc at a much earlier stage of DDD and thereby prevents degradation of the ECM.

Second, since the HAAMMP is specific, it does not inhibit non-targeted cells, tissue or proteins. In addition, the HAAMMP may be combined with other therapeutic agents (such as growth factors or mesenchymal stem cells) that can also be injected into the disc without reducing the effectiveness of those agents.

Third, since the annulus fibrosus portion of the disc comprises a dense fibrosus structure, this outer component of the disc may provide a suitable depot for the HAAMMP, thereby increasing its half-life in the disc.

Accordingly, in one aspect of the present invention, there is provided a method of treating degenerative disc disease in an intervertebral disc having a nucleus pulposus, comprising transdiscally administering a formulation comprising an effective amount of a high affinity anti-matrix metalloproteinase (HAAMMP) into an intervertebral disc.

In some embodiments, the HAAMMP is administered in a formulation comprising a sustained release device.

DETAILED DESCRIPTION OF THE INVENTION

For the purposes of the present invention, the terms "inhibitor" and antagonist" are used interchangeably. A protein may be inhibited at the synthesis level, at the translation level, by shedding, by antibodies, or by soluble receptors. The term "patient" refers to a human having a degenerating disc.

For the purposes of the present invention "transdiscal administration" includes, but is not limited to:
   a) injecting a formulation into the nucleus pulposus of a degenerating disc, such as a relatively intact degenerating disc;
   b) injecting a formulation into the annulus fibrosus of a degenerating disc, such as a relatively intact degenerating disc;
   c) providing a formulation in a patch attached to an outer wall of the annulus fibrosus;
   d) providing a formulation in a depot at a location outside but closely adjacent to an outer wall of the annulus fibrosus ("trans-annular administration"); and
   e) providing a formulation in a depot at a location outside but closely adjacent to an endplate of an adjacent vertebral body (hereinafter, "trans-endplate administration".

Because DDD is a continuous process, the degenerating disc to which the therapeutic drug is administered may be in any one of a number of degenerative states. Accordingly, the degenerating disc may be an intact disc. The degenerating disc may be a herniated disc (i.e., wherein a portion of the annulus fibrosus has a bulge). The degenerating disc may be a ruptured disc (i.e., wherein the annulus fibrosus has ruptured and the bulk nucleus pulposus has exuded). The degenerating disc may be delaminated (i.e., wherein adjacent layers of the annulus fibrosus have separated). The degenerating disc may have fissures (i.e., wherein the annulus fibrosus has fine cracks or tears through which selected molecules from the nucleus pulposus can leak).

The present invention is directed to providing a HAAMMP to a diseased intervertebral disc. In one embodiment, the HAAMMP is administered in an amount effective to inhibit the specific action of MMPs released by disc cells during the degenerative process. In one embodiment, the HAAMMP is administered in an amount effective to inhibit MMPs present in the nucleus pulposus and thereby help arrest degradation of an extracellular matrix.

In one embodiment, the HAAMMP is recombinant. In one embodiment, the HAAMMP is present in an autologous form. The HAAMMP can be present, for example, in an autologous concentrated form.

In some embodiments, the HAAMMP is a natural inhibitor of MMPs, e.g., a tissue inhibitor of MMPs (TIMP). In some embodiments, the TIMP is selected from the group consisting of TIMP-1 and TIMP-2. In some embodiments, the TIMP is autologous and is concentrated by filtration, centrifugation or by immuno-attachment processes. In other embodiments, the TIMP is manufactured recombinantly, and is preferably present in a concentration of, e.g., at least 1000 times that found normally in the patient. In some embodiments, the TIMP can be obtained from a heterologous source.

In some embodiments, the HAAMMP is a specific inhibitor of aggrecanase (i.e., anti-aggrecanase).

In some embodiments, the HAAMMP comprises a chelating group that binds tightly to the zinc component present in the active site of the MMP. Such HAAMMPs may be selected from the materials disclosed in Gordon, *Clin. Exp. Rheumatol.*, 1(Supp 8): S91-4 (1993); and Johnson, J., *Enzyme Inhib.*, 2:1-22 (1987).

In some embodiments, the HAAMMP is a specific antagonist of a collagenase MMP. In some embodiments, the therapeutic substance is a specific antagonist of a stromelysin MMP. In some embodiments, the therapeutic substance is a specific antagonist of a gelatinase MMP. In some embodiments, the therapeutic substance is a specific antagonist of a membrane MMP.

In some embodiments, the targeted MMP is selected from the group consisting MMP-2, MMP-3 and MMP-8. Targeting MMP-2 and/or MMP-3 is desirable because these MMPs are believed to degrade proteoglycans. Targeting MMP-8 is desirable because this MMP is believed to degrade aggrecans.

DDD involves the progressive degeneration of a disc in which many factors are involved. In many instances, simply providing a single dose or even a regimen over the space of a few days may not be sufficient to resolve the DDD. For example, if DDD were caused in part by mechanical instability in a functional spinal unit, then simply providing a one-time therapy for the transdiscal cells would likely only delay the onset of the DDD. Therefore, there is a need to provide a long-term drug therapy treatment of DDD that does not require multiple injections.

Because DDD is a continuous process, it is desirable for the HAAMMP to remain within the nucleus pulposus as long as possible in a pharmaceutically effective amount. The half-life of the HAAMMP within the nucleus pulposus will depend upon many factors, including the size of the HAAMMP and its charge. In general, the larger the molecular weight of the HAAMMP, the more likely it is to remain contained by the annulus fibrosus portion of the disc.

When using a short half-life HAAMMP, it would be desirable for a relatively large dose of the HAAMMP to be administered transdiscally. In this condition, quick depletion of the HAAMMP would not cause the HAAMMP to fall below therapeutically effective levels in the disc until an extended period.

Although a large dose of the HAAMMP would be desirable in such instances, injecting a critical volume of water can increase pressure in the nucleus pulposus. Nociceptors present on the inner wall of the annulus fibrosus react to this increased pressure and produce pain. In some cases, the added amount could be as little as one cc by volume to produce pain. Accordingly, if a dilute concentration of a HAAMMP is added to the nucleus pulposus to provide a large dose, the resulting pressure increase caused by this added volume could be sufficient to cause acute pain.

For example, if it were determined that about 100 mg of a HAAMMP was needed to therapeutically affect a nucleus pulposus, and that HAAMMP was provided in concentrations of from about 30 to about 60 mg/ml, then at least about 1.5 ml of the HAAMMP would need to be injected into the nucleus pulposus in order to provide the desired therapeutic effect. However, when injecting volumes into the nucleus pulposus, it is desirable that the volume of drug delivered be no more than about 1 ml, preferably no more than about 0.5 ml (i.e., a maximum of 0.5 ml.), more preferably between about 0.1 and about 0.3 ml. When injected in these smaller quantities, it is believed the added volume will not cause an appreciable pressure increase in the nucleus pulposus.

Accordingly, in some embodiments, the concentration of the HAAMMP in the administered formulation is at least about 100 mg/ml. When about 100 mg of the HAAMMP is needed to produce the desired therapeutic result, no more than about 1 ml of the drug need be injected. In some embodiments, the concentration of the HAAMMP in the administered drug is at least about 200 mg/ml. In this condition, no more than about 0.5 ml of the drug need be injected. In some embodiments, the concentration of the HAAMMP in the administered drug is at least about 500 mg/ml. In this condition, between about 0.03 to about 0.3 ml of the formulation need be injected.

In some embodiments, the HAAMMP is provided in a sustained release device (i.e., sustained delivery device). The sustained release device is adapted to remain within the disc for a prolonged period and slowly release the HAAMMP contained therein to the surrounding environment. This mode of delivery allows a HAAMMP to remain in therapeutically effective amounts within the disc for a prolonged period.

In some embodiments, the HAAMMP is predominantly released from the sustained delivery device by its diffusion through the sustained delivery device (e.g., through a polymer). In others, the HAAMMP is predominantly released from the sustained delivery device by the biodegradation of the sustained delivery device (e.g., biodegradation of a polymer).

In some embodiments, the sustained release device comprises a bioresorbable material whose gradual erosion causes the gradual release of the HAAMMP to the disc environment. In some embodiments, the sustained release device comprises a bioresorbable polymer. In some embodiments, the bioresorbable polymer has a half-life of at least one month, more preferably at least two months, more preferably at least 6 months.

In some embodiments, the sustained delivery device comprises bioerodable macrospheres. The HAAMMP is preferably contained in a gelatin (or water or other solvent) within the capsule, and is released to the disc environment when the outer shell has been eroded. The device can include a plurality of capsules having outer shells of varying thickness, so that the sequential breakdown of the outer shells provides periodic release of the HAAMMP.

In some embodiments, the sustained release device provides controlled release. In some embodiments, it provides continuous release. In some embodiments, it provides intermittent release. In some embodiments, the sustained release device comprises a biosensor. Other release modes may also be used.

In some embodiments, the sustained delivery device comprises an inflammatory-responsive delivery system, such as one comprising bioerodable microspheres that are eroded by invading macrophages. This technology provides a high correspondence between physiologic inflammation of disc environment and the release of the HAAMMPs into that environment. In one embodiment, the technology disclosed in Brown et al., *Arthritis. Rheum.* Dec., 41(12): 2185-95 (1998) is selected.

In some embodiments, the sustained delivery device comprises the devices disclosed in U.S. Pat. No. 5,728,396 ("Peery"), the specification of which is incorporated by reference in its entirety.

In some embodiments, the sustained delivery device comprises a plurality (e.g., at least one hundred) of water-containing chambers, each chamber containing the HAAMMP. A chamber is defined by bilayer lipid membranes comprising synthetic duplicates of naturally occurring lipids. Release of the drug can be controlled by varying at least one of the aqueous excipients, the lipid components, and the manufacturing parameters. Preferably, the formulation comprises no more than 10% lipid. In some embodiments, the Depofoam™ technology of Skyepharma PLC (London, United Kingdom) is selected.

In some embodiments, the sustained delivery device comprises a delivery system disclosed in U.S. Pat. No. 5,270,300 ("Hunziker"), the specification of which is incorporated by reference in its entirety.

In some embodiments, the sustained delivery device comprises the co-polymer poly-DL-lactide-co-glycolide (PLG). Preferably, the formulation is manufactured by combining the HAAMMP or additional therapeutic agent, the co-polymer and a solvent to form a droplet, and then evaporating the solvent to form a microsphere. The plurality of microspheres are then combined in a biocompatible diluent. Preferably, the HAAMMP or additional therapeutic agent is released from the co-polymer by its diffusion therethrough and by the biodegradation of the co-polymer. In some embodiments hereof, the ProLease™ technology of Alkermes (located in Cambridge, Mass.) is selected.

In some preferred embodiments, the HAAMMP is combined in the formulation with a sustained release device comprising a viscosupplement. The viscosupplement has a viscosity and elasticity substantially similar to that of natural healthy nucleus pulposus.

Preferably, the viscosupplement is selected from the group consisting of hyaluronic acid and hyaluronate (either crosslinked or uncross-linked). In some embodiments, the viscosupplement is Arthrease™ (DePuy Ltd., Leeds, U.K.). In some embodiments, the viscosupplement is a hyaluronic acid selected from the hyaluronic acids disclosed in U.S. Ser. No. 09/298,539, entitled "Method of Treating Diseased, Injured or Abnormal Cartilage with Hyaluronic Acid and Growth Factors"(Radomsky et al.), the specification of which is incorporated by reference in its entirety.

Hydrogels can also be used to deliver the HAAMMP in a sustained release manner to the disc environment. A "hydrogel" is a substance formed when an organic polymer (natural or synthetic) is set or solidified to create a three-dimensional open-lattice structure that entraps molecules of water or other solution to form a gel. The solidification can occur, e.g., by aggregation, coagulation, hydrophobic interactions, or crosslinking. The hydrogels employed in this invention can rapidly solidify to keep the HAAMMP at the application site, thereby eliminating undesired migration from the disc. The hydrogels are also biocompatible, e.g., not toxic, to cells suspended in the hydrogel.

A "hydrogel-HAAMMP composition" is a suspension of a hydrogel containing HAAMMP. The hydrogel-HAAMMP composition forms a uniform distribution of HAAMMP with a well-defined and precisely controllable density. Moreover, the hydrogel can support very large densities of HAAMMP. In addition, the hydrogel allows diffusion of nutrients to, and waste products away from, the endplates, which promotes tissue growth.

Hydrogels suitable for use in the present invention include water-containing gels, i.e., polymers characterized by hydrophilicity and insolubility in water. See, for instance, "Hydrogels", pages 458-459 in *Concise Encyclopedia of Polymer Science and Engineering*, Eds. Mark et al., Wiley and Sons (1990), the disclosure of which is incorporated herein by reference in its entirety. Although their use is optional in the present invention, the inclusion of hydrogels is can be highly advantageous since they tend to possess a number of desirable qualities. By virtue of their hydrophilic, water-containing nature, hydrogels can:

a) house viable cells, such as mesenchymal stems cells, and
b) assist with load bearing capabilities of the disc.

In one embodiment, the hydrogel is a fine, powdery synthetic hydrogel. Suitable hydrogels exhibit an optimal combination of such properties as compatibility with the matrix polymer of choice, and biocompatability. The hydrogel can include any one or more of the following: polysaccharides, proteins, polyphosphazenes, poly(oxyethylene)-poly(oxyproplene) block polymers, poly(oxyethylene)-poly(oxypropylene) block polymers of ethylene diamine, poly(acrylic acids), poly(methacrylic acids), copolymers of acrylic acid and methacrylic acid, poly(vinyl acetate), and sulfonated polymers.

In general, these polymers are at least partially soluble in aqueous solutions, e.g., water, or aqueous alcohol solutions that have charged side groups, or a monovalent ionic salt thereof. There are many examples of polymers with acidic side groups that can be reacted with cations, e.g., poly(phosphazenes), poly(acrylic acids), and poly(methacrylic acids). Examples of acidic groups include carboxylic acid groups, sulfonic acid groups, and halogenated (preferably fluorinated) alcohol groups. Examples of polymers with basic side groups that can react with anions are poly(vinyl amines), poly(vinyl pyridine), and poly(vinyl imidazole).

In some embodiments, the sustained delivery device includes a polymer selected from the group consisting of PLA, PGA, PCL and mixtures thereof.

When using a relatively long-half life HAAMMP, a relatively small dose of the HAAMMP can be administered into the disc. In this condition, the slow depletion of the HAAMMP would not cause the HAAMMP to fall below therapeutically effective levels in the disc until an extended period of time has elapsed.

In some embodiments in which HAAMMP have long half-lives within the disc space, the dose administered can be very small.

For example, if it is believed that an HAAMMP is effective when present in the range of about 1 to about 10 mg/kg or from about 1 to about 10 ppm, and since a typical nucleus pulposus of a disc has a volume of about 3 ml (or 3 cc, or 3 g), then only about 3 to about 30 ug of the HAAMMP need be administered to the disc in order to provide a long lasting effective amount of the HAAMMP. The formulation can be administered in an amount of less than 1 cc. As a point of reference, Tobinick discloses that at least 1 mg of cytokine antagonist should be administered perispinally in order to cure back pain. The smaller amounts available by this route reduce the chances of deleterious side effects of the HAAMMP.

For example, if a clinician administered 0.3 ml of 60 mg/ml HAAMMP into a 2.7 cc disc, this would produce a HAAMMP concentration in the disc of about 6 mg/ml, or 6 parts per thousand. Without wishing to be tied to a theory, if HAAMMP has the same half-life within a nucleus pulposus as it does when administered systemically (i.e, about 1 week), then the concentration of HAAMMP would remain above about 10 ppm for about 9 weeks. Therefore, if another dose were needed, the clinician would only need to provide the second dose after about two months.

Therefore, in some embodiments, the HAAMMP is provided in a dose of less than about 1 mg, e.g., less than about 0.5 mg, more preferably, less than about 0.1 mg, more preferably less than about 0.01 mg, more preferably less than about 0.001 mg. The smaller amounts available by this route reduce the chances of deleterious side effects of the HAAMMP.

In some embodiments, the formulation of the present invention is administered directly into the disc through the outer wall of the annulus fibrosus. More preferably, the direct administration includes depositing the HAAMMP in the nucleus pulposus portion of the disc. In this condition, the fibrous nature of the annulus fibrosus that surrounds the nucleus pulposus will help keep the HAAMMP contained within the disc.

In some embodiments, the formulation of the present invention is injected into the disc through a small bore needle. In some embodiments, the needle has a bore of about 22 gauge or less, so that the possibilities of producing a herniation are mitigated. For example, the needle can have a bore of about 24 gauge or less, so that the possibilities of producing a herniation are even further mitigated.

If the volume of the direct injection of the formulation is sufficiently high so as to cause a concern of overpressurizing the nucleus pulposus, then it is preferred that at least a portion of the nucleus pulposus be removed prior to direct injection. In some embodiments, the volume of removed nucleus pulposus is substantially similar to the volume of the formulation to be injected. For example, the volume of removed nucleus pulposus can be within 80-120% of the volume of the formulation to be injected. In addition, this procedure has the added benefit of at least partially removing some degenerated disc from the patient.

In other embodiments, the formulation is delivered into the disc space through the endplate of an opposing vertebral body. This avenue eliminates the need to puncture the annulus fibrosus, and so eliminates the possibility of herniation.

Although the HAAMMP may therapeutically treat the disc by binding an MMP, thereby reducing pain and arresting degradation of the ECM, it is believed that at least some of these HAAMMPs do not help repair the damage done by the MMP to the ECM.

Therefore, there may be a need to provide a therapy that also helps repair the ECM.

In accordance with the present invention, there is provided a method of treating degenerative disc disease in an intervertebral disc having a nucleus pulposus, comprising:
 a) transdiscally administering HAAMMP into a degenerating disc; and
 b) transdiscally administering at least one additional therapeutic agent in an amount effective to at least partially repair the disc (i.e., the disc tissue).

In accordance with one aspect of the invention, both the HAAMMP and at least one additional therapeutic agent are locally administered into the disc space. There can be, for example, one additional therapeutic agent (i.e., a second therapeutic agent) or there can be multiple additional therapeutic agents (e.g., second and third therapeutic agents).

In some embodiments, the HAAMMP and additional therapeutic agent (i.e., additional therapeutic substance) are administered simultaneously. In others, the HAAMMP is administered first. In still other, the second therapeutic agent is administered first.

Other compounds which may be added to the disc include, but are not limited to: vitamins and other nutritional supplements; hormones; glycoproteins; fibronectin; peptides and proteins; carbohydrates (both simple and/or complex); proteoglycans; oligonucleotides (sense and/or antisense DNA and/or RNA); bone morphogenetic proteins (BMPs); antibodies (for example, to infectious agents, tumors, drugs or hormones); gene therapy reagents; and anti-cancer agents. Genetically altered cells and/or other cells may also be included in the matrix of this invention. If desired, substances such as pain killers and narcotics may also be admixed with the polymer for delivery and release to the disc space.

Healthy cells can be introduced into the disc that can at least partially repair any damage done to the disc during the degenerative process. In some embodiments, these cells are introduced into the nucleus pulposus and ultimately produce new extracellular matrix for the nucleus pulposus. In others, these cells are introduced into the annulus fibrosus and produce new extracellular matrix for the annulus fibrosus.

In some embodiments, these cells are obtained from another human individual (allograft), while in other embodiments, the cells are obtained from the same individual (autograft). In some embodiments, the cells are taken from an intervertebral disc (for example, either nucleus pulposus cells or annulus fibrosus cells), while in other embodiments, the cells are taken from a non-disc tissue (for example, mesenchymal stem cells or chondrocytes). In other embodiments, autograft chondrocytes (such as from the knee, hip, shoulder, finger or ear) may be used.

In one embodiment, when viable cells are selected as the additional therapeutic substance, the viable cells comprise mesenchymal stem cells (MSCs). MSCs provide a special advantage for administration into a degenerating disc because it is believed that they can more readily survive the relatively harsh environment present in the degenerating disc; that they have a desirable level of plasticity; and that they have the ability to proliferate and differentiate into the desired cells.

In some embodiments, the mesenchymal stem cells are obtained from bone marrow, preferably autologous bone marrow. In others, the mesenchymal stem cells are obtained from adipose tissue, preferably autologous adipose tissue.

In some embodiments, the mesenchymal stem cells injected into the disc are provided in an unconcentrated form. In other embodiments, they are provided in a concentrated form. When provided in concentrated form, they can be uncultured. Uncultured, concentrated MSCs can be readily obtained by centrifugation, filtration, or immunoabsorption. When filtration is selected, the methods disclosed in U.S. Pat. No. 6,049,026 ("Muschler"), the specification of which is incorporated by reference in its entirety, are preferably used. In some embodiments, the matrix used to filter and concentrate the MSCs is also administered into the nucleus pulposus. If this matrix has suitable mechanical properties, it can be used to restore the height of the disc space that was lost during the degradation process.

In some embodiments, growth factors are additional therapeutic agents. As used herein, the term "growth factors" encompasses any cellular product that modulates the growth or differentiation of other cells, particularly connective tissue progenitor cells. The growth factors that may be used in accordance with the present invention include, but are not limited to, members of the fibroblast growth factor family, including acidic and basic fibroblast growth factor (FGF-1 and -2) and FGF-4, members of the platelet-derived growth factor (PDGF) family, including PDGF-AB, PDGF-BB and PDGF-AA; EGFs, members of the insulin-like growth factor (IGF) family, including IGF-I and -II; the TGF-$\beta$ superfamily, including TGF-$\beta$1, 2 and 3 (including MP-52), osteoid-inducing factor (OIF), angiogenin(s), endothelins, hepatocyte growth factor and keratinocyte growth factor; members of the bone morphogenetic proteins (BMPs) BMP-1; BMP-3; BMP-2; OP-1; BMP-2A, -2B, -4, -7 and -14; HBGF-1 and HBGF-2; growth differentiation factors (GDFs), members of the hedgehog family of proteins, including indian, sonic and desert hedgehog; ADMP-1; GDF-5; and members of the colony-stimulating factor (CSF) family, including CSF-1, G-CSF, and GM-CSF; and isoforms thereof.

In some embodiments, the growth factor is selected from the group consisting of TGF-$\beta$, bFGF, and IGF-1. These growth factors are believed to promote regeneration of the nucleus pulposus, or stimulate proliferation and/or differentiation of chondrocytes, as well as ECM secretion. In one embodiment, the growth factor is TGF-$\beta$. More preferably, TGF-$\beta$ is administered in an amount of between about 10 ng/ml and about 5000 ng/ml, for example, between about 50 ng/ml and about 500 ng/ml, e.g., between about 100 ng/ml and about 300 ng/ml.

In some embodiments, platelet concentrate is provided as an additional therapeutic agent. In one embodiment, the growth factors released by the platelets are present in an amount at least two-fold (e.g., four-fold) greater than the amount found in the blood from which the platelets were taken. In some embodiments, the platelet concentrate is autologous. In some embodiments, the platelet concentrate is platelet rich plasma (PRP). PRP is advantageous because it contains growth factors that can restimulate the growth of the ECM, and because its fibrin matrix provides a suitable scaffold for new tissue growth.

In some embodiments, an additional therapeutic substance is a high specificity cytokine antagonist ("HSCA"). For example, the high affinity cytokine antagonist is selected from the group consisting of an HSCA of TNF-α, and an HSCA of an interleukin.

In some embodiments, the HSCA is a specific antagonist of TNF-α. Preferred TNF antagonists include, but are not limited to, the following: etanercept (Enbrel® Amgen); infliximab (Remicade® Johnson and Johnson); D2E7, a human anti-TNF monoclonal antibody (Knoll Pharmaceuticals, Abbott Laboratories); CDP 571 (a humanized anti-TNF IgG4 antibody); CDP 870 (an anti-TNF alpha humanized monoclonal antibody fragment), both from Celltech; soluble TNF receptor Type I (Amgen); pegylated soluble TNF receptor Type I (PEGs TNF-R1) (Amgen); and onercept, a recombinant TNF binding protein (r-TBP-1) (Serono).

In some embodiments, the HSCA is a specific antagonist of an interleukin. Preferably, the target interleukin is selected from the group consisting IL-1, IL-2, IL-6 and IL-8, and IL-12. Preferred antagonists include but are not limited to Kineretg (recombinant IL 1-RA, Amgen), IL1-Receptor Type 2 (Amgen) and IL-1 Trap (Regeneron).

Since many pro-inflammatory proteins play a role in disc degeneration, and that the antagonists of the present invention are highly specific, it is further believed that injecting at least two of the highly specific antagonists of the present invention directly into the disc would be advantageous.

Therefore, in accordance with the present invention, there is provide a method of treating degenerative disc disease in an intervertebral disc having a nucleus pulposus, comprising administering a formulation comprising HAAMMP and at least two highly specific antagonists of pro-inflammatory cytokines selected from the group consisting of TNF-α, an interleukin (preferably, IL-1, IL-6 and IL-8), FAS, an FAS ligand, and IFN-gamma.

In one embodiment, at least one of the therapeutic agents is an antagonist of TNF-α. In one embodiment, another therapeutic agent is an antagonist of an interleukin.

In some embodiments, the formulation comprises a suitable biocompatible carrier such as saline. In some embodiments, the carrier is selected from the carriers disclosed in U.S. Pat. No. 6,277,969 ("Le"), the specification of which is incorporated by reference in its entirety.

Also in accordance with the present invention, there is provided a kit comprising a device containing:
a) a HAAMMP; and
b) at least one additional therapeutic agent comprising MSCs present in an amount effective to at least partially repair a degenerating disc.

Also in accordance with the present invention, there is provided a formulation for treating degenerative disc disease, comprising:
a) HAAMMP, and
b) at least one additional therapeutic agent selected from the group consisting of:
  i) a growth factor, and
  ii) viable cells.

Because the causes of low back pain may be myriad, and because of the significant cost of some HAAMMPs, it would be useful for a clinician to first perform a diagnostic test in order to confirm that the targeted disc in fact possesses high levels of the targeted MMPs prior to providing the injection.

In one embodiment, the diagnostic test comprises a non-invasive diagnostic test comprising, for example, using an MRI. In some embodiments, the MRI is able to quantify the aggrecans levels within the disc.

In one embodiment, the clinician would first perform a discogram in order to identify which disc or discs are responsible for the patient's low back pain. Next, the clinician would perform an invasive or non-invasive test upon the targeted disc in order to confirm the presence of or quantify the level of the MMPs.

It is further believed that the present invention can also be used to prevent degeneration of an intervertebral disc in a human individual, namely, by following a procedure comprising:
a) determining a genetic profile of the individual;
b) comparing the profile of the individual against a predetermined genetic profile level of at-risk humans;
c) determining that the individual is an at-risk patient; and
d) injecting an HAAMMP into a disc of the individual.

It is further believed that transdiscal administration of an effective amount of other high specificity antagonists of pro-inflammatory compounds would also help provide therapy to the patient having DDD. In many embodiments, the transdiscal administration is of an effective amount of a high specificity antagonist of an enzyme.

It is further believed that transdiscal administration of an effective amount of a high specificity antagonist of p38 kinase would also help provide therapy to the patient having DDD. It is believed that the p38 kinase site regulates the production of TNF-α, IL-1 and COX-2 enzyme. Therefore, in accordance with another embodiment of the present invention, there is provided a method of treating degenerative disc disease in an intervertebral disc having a nucleus pulposus, comprising transdiscally administering an effective amount of a formulation comprising a high affinity antagonist of p 38 kinase into an intervertebral disc.

Some high specificity antagonists of p 38 kinase are disclosed in Zhang, *J Biol. Chem.*, 272(20), May 16, 1997 (13397-402); Pargellis, *Nature Structural Biology*, 9(4), April 2002268-272, and Chae, *Bone*, 28(1), 45-53 (January 2001), and in U.S. Pat. No. 6,541,477 ("Goehring"), the specification of which is hereby incorporated by reference in its entirety.

It is further believed that transdiscal administration of an effective amount of a high specificity antagonist of the COX-2 enzyme would also help provide therapy to the patient having DDD. It is believed that the COX-2 enzyme is a regulator of the production of prostaglandins, which are involved both in inflammation and the generation of pain. Therefore, in accordance with another embodiment of the present invention, there is provided a method of treating degenerative disc disease in an intervertebral disc having a nucleus pulposus, comprising transdiscally administering an effective amount of a formulation comprising a high affinity antagonist of COX-2 enzyme into an intervertebral disc.

Typical high specificity antagonists of the COX-2 enzyme include Celecoxib (Searle), Rofecoxib (Merck); Meloxican (Boehringer Manheim); Nimesulide; diclofenac and Lodine.

It is further believed that transdiscal administration of an effective amount of a high specificity antagonist of the $PLA_2$ enzyme would also help provide therapy to the patient having DDD. It is believed that the $PLA_2$ enzyme is a regulator of the production of prostaglandin. Therefore, in accordance with another embodiment of the present invention, there is provided a method of treating degenerative disc disease in an intervertebral disc having a nucleus pulposus, comprising transdiscally administering an effective amount of a formulation comprising a high affinity antagonist of $PLA_2$ enzyme into an intervertebral disc. In some embodiments, the high specificity antagonist of PLA2 may be administered systemically.

At least one high specificity antagonist of $PLA_2$ is disclosed in Kawakami, *Clin. Orthop.*, 351: 241-51 (1998).

It is further believed that transdiscal administration of an effective amount of a high specificity antagonist of the NO synthase enzyme would also help provide therapy to the patient having DDD. It is believed that the NO synthase enzyme regulates the production of NO, which is known to have pro-inflammatory effects. Therefore, in accordance with another embodiment of the present invention, there is provided a method of treating degenerative disc disease in an intervertebral disc having a nucleus pulposus, comprising transdiscally administering an effective amount of a formulation comprising a high affinity antagonist of NO synthase into an intervertebral disc. In some embodiments, the high specificity antagonists of NO synthase may be administered systemically.

Some high specificity antagonists of NO synthase are N-iminoethyl-L-lysine (L-NIL), and $N^G$-monomethyl-L-arginine.

It is further believed that transdiscal administration of an effective amount of a high specificity anti-oxidant would also help provide therapy to the patient having DDD. It is believed that oxidants degrade the nucleus pulposus extra-cellular matrix. Typical anti-oxidants include free radical scavengers and superoxide dismutase enzymes. Therefore, in accordance with another embodiment of the present invention, there is provided a method of treating degenerative disc disease in an intervertebral disc having a nucleus pulposus, comprising transdiscally administering an effective amount of a formulation comprising a high affinity antioxidant into an intervertebral disc. In some embodiments, the high specificity anti-oxidants may be administered systemically.

EXAMPLE I

This non-limiting prophetic example describes how to transdiscally administer a formulation comprising an HAAMMP and saline into a nucleus pulposus of a degenerating disc.

First, a clinician uses a diagnostic test to verify that a particular disc within a patient has high levels of MMPs.

Next, the clinician provides a local anesthetic (such as 5 ml lidocaine) to the region dorsal of the disc of concern to reduce subcutaneous pain.

Next, the clinician punctures the skin of the patient dorsal the disc of concern with a relatively large (e.g., 18-19 gauge) needle having a stylet therein, and advances the needle through subcutaneous fat and dorsal sacrolumbar ligament and muscles to the outer edge of the intervertebral disc.

Next, the stylet is removed from the needle.

Next, the clinician receives a syringe having a smaller gauge needle adapted to fit within the larger gauge needle. This needle is typically a 22 or 24 gauge needle. The barrel of the syringe contains the formulation of the present invention.

The formulation contains an HAAMMP, and has an HAAMMP concentration of between about 30 mg/ml and about 60 mg/ml.

Next, the physician advances the smaller needle co-axially through the larger needle and past the distal end of the larger needle, thereby puncturing the annulus fibrosus. The smaller needle is then further advanced into the center of the nucleus pulposus. Finally, the clinician depresses the plunger of the syringe, thereby injecting between about 0.1 and 1 ml of the formulation into the nucleus pulposus.

EXAMPLE II

This non-limiting prophetic example is substantially similar to that of Example I, except that the formulation comprises a sustained release device comprising the co-polyer poly-DL-lactide-co-glycolide (PLG). The formulation contains HAAMMP as the antagonist, and has an HAAMMP concentration of between about 30 mg/ml and about 60 mg/ml.

What is claimed is:

1. A method of treating degenerative disc disease in an intervertebral disc having a nucleus pulposus, comprising transdiscally administering an effective amount of a formulation comprising tissue inhibitor of matrix metalloproteinase-1 (TIMP-1) into an intervertebral disc, wherein the TIMP-1 is a recombinant TIMP-1, and wherein said administering is performed through a needle.

2. A method of treating degenerative disc disease in an intervertebral disc having a nucleus pulposus, comprising transdiscally administering an effective amount of a formulation comprising a tissue inhibitor of matrix metalloproteinase (TIMP) into an intervertebral disc, wherein the TIMP is present in an autologous concentrated form, and wherein said TIMP is selected from the group consisting of TIMP-1 and TIMP-2, and wherein said administering is performed through a needle.

3. A method of treating degenerative disc disease in an intervertebral disc having a nucleus pulposus, comprising transdiscally administering an effective amount of a formulation comprising a tissue inhibitor of matrix metalloproteinase (TIMP) into an intervertebral disc, wherein said TIMP is selected from the group consisting of TIMP-1 and TIMP-2, and wherein said administering is performed through a needle, and wherein the formulation is administered in a volume of between 0.03 ml and 0.3 ml.

4. A method of treating degenerative disc disease in an intervertebral disc having a nucleus pulposus, comprising transdiscally administering a formulation comprising a tissue inhibitor of matrix metalloproteinase (TIMP) into an intervertebral disc, wherein said TIMP is selected from the group consisting of TIMP-1 and TIMP-2, and wherein said administering is performed through a needle in an amount effective to inhibit matrix metalloproteinases (MMPs) present in the nucleus pulposus and help arrest degradation of an extracellular matrix, and wherein the concentration of TIMP in the formulation is at least 100 mg/ml.

5. A method of treating degenerative disc disease in an intervertebral disc having a nucleus pulposus, comprising transdiscally administering an effective amount of a formulation comprising a tissue inhibitor of matrix metalloproteinase (TIMP) into an intervertebral disc, wherein said TIMP is selected from the group consisting of TIMP-1 and TIMP-2, and wherein said administering is performed through a needle, and wherein the formulation further comprises at least one additional therapeutic agent.

6. A method of treating degenerative disc disease in an intervertebral disc having a nucleus pulposus, comprising transdiscally administering an effective amount of a formulation comprising a tissue inhibitor of matrix metalloproteinase (TIMP) into an intervertebral disc, wherein said TIMP is selected from the group consisting of TIMP-1 and TIMP-2, and wherein said administering is performed through a needle, and wherein the formulation is administered in an amount of less than 1 cc.

7. The method of claim 6 wherein the concentration of TIMP in the formulation is at least 100 mg/ml.

8. A method of treating degenerative disc disease in an intervertebral disc having a nucleus pulposus, comprising transdiscally administering an effective amount of a formulation comprising a tissue inhibitor of matrix metalloproteinase (TIMP) into an intervertebral disc, wherein said TIMP is selected from the group consisting of TIMP-1 and TIMP-2, and wherein said administering is performed through a needle, and wherein the formulation further comprises a sustained release device.

9. The method of claim 8 wherein the sustained release device comprises a hydrogel.

10. The method of claim 8 wherein the sustained release device provides controlled release.

11. The method of claim 8 wherein the sustained release device provides continuous release.

12. The method of claim 8 wherein the sustained release device provides intermittent release.

13. The method of claim 8 wherein the sustained release device comprises a biosensor.

14. The method of claim 8 wherein the sustained release device comprises microspheres.

15. The method of claim 8 wherein the TIMP is predominantly released from the sustained delivery device by diffusion through the sustained delivery device or by biodegradation of the sustained delivery device.

16. The method of claim 8 wherein the sustained release device comprises an inflammatory-responsive delivery system.

17. A method of treating degenerative disc disease in an intervertebral disc having a nucleus pulposus, comprising transdiscally administering an effective amount of a formulation comprising a tissue inhibitor of matrix metalloproteinase (TIMP) into an intervertebral disc, and wherein said TIMP is selected from the group consisting of TIMP-1 and TIMP-2, and wherein said administering is performed through a needle, and wherein the TIMP is present in the formulation in a maximum amount of about 0.5 mg.

18. A method of treating degenerative disc disease in an intervertebral disc having a nucleus pulposus, comprising transdiscally administering an effective amount of a formulation comprising a tissue inhibitor of matrix metalloproteinase (TIMP) into an intervertebral disc, wherein said TIMP is selected from the group consisting of TIMP-1 and TIMP-2, and wherein said administering is performed through a needle, and wherein the formulation further comprises a growth factor is provided by platelet concentrate, said growth factor present in an amount effective to repair disc tissue.

19. A method of treating degenerative disc disease in an intervertebral disc having a nucleus pulposus, comprising transdiscally administering an effective amount of a formulation comprising a tissue inhibitor of matrix metalloproteinase (TIMP) into an intervertebral disc, wherein said TIMP is selected from the group consisting of TIMP-1 and TIMP-2, and wherein said administering is performed through a needle, and wherein the formulation further comprises viable mesenchymal stem cells.

20. A method of treating degenerative disc disease in an intervertebral disc having a nucleus pulposus, comprising transdiscally administering an effective amount of a formulation comprising a tissue inhibitor of matrix metalloproteinase (TIMP) into an intervertebral disc, wherein said TIMP is selected from the group consisting of TIMP-1 and TIMP-2, and wherein said administering is performed through a needle, and wherein the formulation is injected into the nucleus pulposus.

21. A method of treating degenerative disc disease in an intervertebral disc having a nucleus pulposus, comprising transdiscally administering an effective amount of a formulation comprising a tissue inhibitor of matrix metalloproteinase (TIMP) into an intervertebral disc, wherein said TIMP is selected from the group consisting of TIMP-1 and TIMP-2, and wherein said administering is performed through a needle, and wherein the formulation is injected into the annulus fibrosus.

22. A method of treating degenerative disc disease in an intervertebral disc having a nucleus pulposus, comprising transdiscally administering an effective amount of a formulation comprising a tissue inhibitor of matrix metalloproteinase (TIMP) into an intervertebral disc, wherein said TIMP is selected from the group consisting of TIMP-1 and TIMP-2, and wherein said administering is performed through a needle, and wherein a portion of the nucleus pulposus is removed prior to administering the formulation into the intervertebral disc.

23. A method of treating degenerative disc disease in an intervertebral disc having a nucleus pulposus, comprising transdiscally administering an effective amount of a formulation comprising a tissue inhibitor of matrix metalloproteinase (TIMP) into an intervertebral disc, wherein said TIMP is selected from the group consisting of TIMP-1 and TIMP-2, and wherein said administering is performed through a needle, and wherein the degenerating disc is an intact disc.

24. A method of treating degenerative disc disease in an intervertebral disc having a nucleus pulposus, comprising transdiscally administering an effective amount of a formulation comprising a tissue inhibitor of matrix metalloproteinase (TIMP) into an intervertebral disc, wherein said TIMP is selected from the group consisting of TIMP-1 and TIMP-2, and wherein said administering is performed through a needle, and wherein the degenerating disc is a ruptured disc.

25. A method of treating degenerative disc disease in an intervertebral disc having a nucleus pulposus, comprising transdiscally administering an effective amount of a formulation comprising a tissue inhibitor of matrix metalloproteinase (TIMP) into an intervertebral disc, wherein said TIMP is selected from the group consisting of TIMP-1 and TIMP-2, and wherein said administering is performed through a needle, and wherein the degenerating disc is delaminated.

26. A method of treating degenerative disc disease in an intervertebral disc having a nucleus pulposus, comprising transdiscally administering an effective amount of a formulation comprising a tissue inhibitor of matrix metalloproteinase (TIMP) into an intervertebral disc, wherein said TIMP is selected from the group consisting of TIMP-1 and TIMP-2, and wherein said administering is performed through a needle, and wherein the degenerating disc has fissures.

27. A method of treating degenerative disc disease in an intervertebral disc having a nucleus pulposus, comprising transdiscally administering an effective amount of a formulation comprising a tissue inhibitor of matrix metalloproteinase (TIMP) into an intervertebral disc, wherein said TIMP is selected from the group consisting of TIMP-1 and TIMP-2, and wherein said administering is performed through a needle, and wherein the TIMP is predominantly released from a sustained delivery device by diffusion of the TIMP through the sustained delivery device.

28. The method of claim 27 wherein the sustained delivery device is a polymer.

29. A method of treating degenerative disc disease in an intervertebral disc having a nucleus pulposus, comprising transdiscally administering an effective amount of a formulation comprising tissue inhibitor of matrix metalloproteinase-2 (TIMP-2) into an intervertebral disc, wherein the TIMP-2 is a recombinant TIMP-2, and wherein said administering is performed through a needle.

* * * * *